United States Patent [19]

Nakamura et al.

[11] Patent Number: 4,810,640

[45] Date of Patent: Mar. 7, 1989

[54] METHOD OF QUANTITATIVE ASSAY FOR 1,5-ANHYDROGLUCITOL

[75] Inventors: Tsuneo Nakamura, Saitama; Hiroshi Akanuma, Kanagawa; Akinori Naito; Masahiko Yabuuchi, both of Saitama; Akira Takahashi, Tokyo; Shigeru Tajima; Masashi Hashiba, both of Gunma; Kazuo Kato, Saitama, all of Japan

[73] Assignee: Nippon Kayaku Kabushiki Kaisha, Tokyo, Japan

[21] Appl. No.: 867,088

[22] Filed: May 27, 1986

[30] Foreign Application Priority Data

May 28, 1985 [JP] Japan .............................. 60-113100
Feb. 28, 1986 [JP] Japan .............................. 61-41404

[51] Int. Cl.⁴ .............................................. C12Q 1/26
[52] U.S. Cl. ...................................... 435/25; 435/26; 435/28; 435/105; 435/810; 435/817
[58] Field of Search .................. 435/25, 28, 105, 817, 435/810, 26

[56] References Cited

FOREIGN PATENT DOCUMENTS

2907628 5/1980 Fed. Rep. of Germany .
1516338 7/1978 United Kingdom .

OTHER PUBLICATIONS

Yoshioka–I Clinical Chem. 28(6), pp. 1283–1286, (1982).
Yoshioka–II Clinical Chem. 29(7), pp. 1396–1398, (1983).
Chemical Abstracts, vol. 104, No. 25, p. 267, 221138u, Jun. 23, 1986.
Chemical Abstracts, vol. 97, No. 11, p. 400, 88208k, Sep. 13, 1982.
Chemical Abstracts, vol. 95, No. 7, p. 485, 59449t, Aug. 17, 1981.
Chemical Abstracts, vol. 92, No. 15, p. 300, 124304w. Apr. 14, 1980.

*Primary Examiner*—Robert J. Warden
*Assistant Examiner*—Robert Benson
*Attorney, Agent, or Firm*—Henry C. Nields

[57] ABSTRACT

The present invention relates to a method of quantitative assay for 1,5-anhydroglucitol which comprises oxidizing 1,5-anhydroglucitol in an aqueous solution of a specimen in the presence of an electron acceptor to produce a compound represented by formula (1) below or a hydrate thereof represented by formula (2) below and quantitatively determining 1,5-anhydroglucitol from a consumption amount of said electron acceptor in said aqueous solution of a specimen or from a production amount of the reduction product of said electron acceptor produced or from an amount of oxidized product of 1,5-AG represented by formula (1) or formula (2).

7 Claims, 4 Drawing Sheets

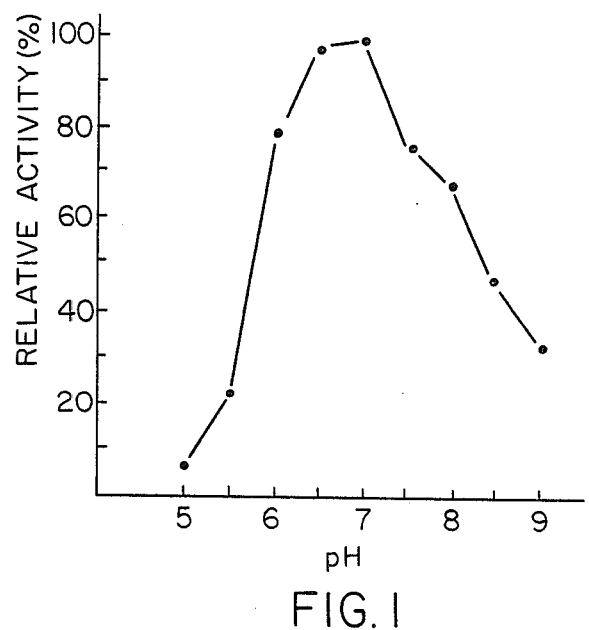
FIG. I
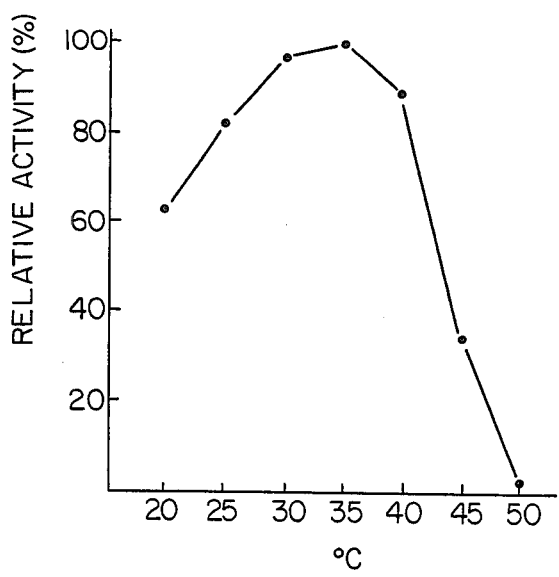
FIG. 2

METHOD OF QUANTITATIVE ASSAY FOR 1,5-ANHYDROGLUCITOL

FIELD OF THE INVENTION

The present invention relates to a method of quantitative assay for 1,5-anhydroglucitol (hereafter referred to as "1,5-AG") which is expected as a marker for diagnosis of diabetes.

BACKGROUND OF THE INVENTION 1,5-AG is a compound which is present in the cerebrospinal fluid and plasma of humans and it is reported that its quantity is reduced in plasma with certain diseases, particularly with diabetes. It has not been known the presence of an enzyme that oxidizes this 1,5-AG. The assay for 1,5-AG has been hitherto performed mainly based on gas chromatography (J. Biochem., 90, 157–162 (1981)).

However, the prior art method requires techniques for pretreatment of specimen and maintenance and control of analysis equipment to high degree and a simple method of assay for 1,5-AG has been demanded.

SUMMARY OF THE INVENTION

The present invention is based on novel findings that 1,5-AG is oxidized in the presence of an electron acceptor to produce a compound represented by formula (1) below:

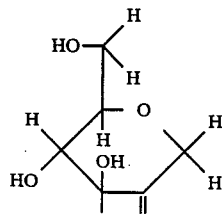

(1)

and this compound is easily hydrated in water to produce a compound represented by formula (2) below:

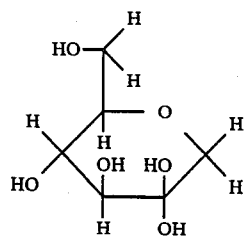

(2)

Namely, the present invention relates to a method of quantitative assay for 1,5-anhydroglucitol which comprises oxidizing 1,5-anhydroglucitol in an aqueous solution of a specimen in the presence of an electron acceptor to produce a compound represented by formula (1) above or a hydrate thereof represented by formula (2) above and quantitatively determining 1,5-anhydroglucitol from a comsumption amount of said electron acceptor in said aqueous solution of a specimen, from a production amount of the reduction product of said electron acceptor produced or from an amount of an oxidized product of 1,5-AG represented by formula (1), or formula (2).

BRIEF DESCRIPTION OF THE DRAWINGS

FIG. 1 is a curve showing the optimum pH of an enzyme used in the present invention;

FIG. 2 is a curve showing the optimum temperature of the enzyme;

DETAILED DESCRIPTION OF THE INVENTION

Figure 3:
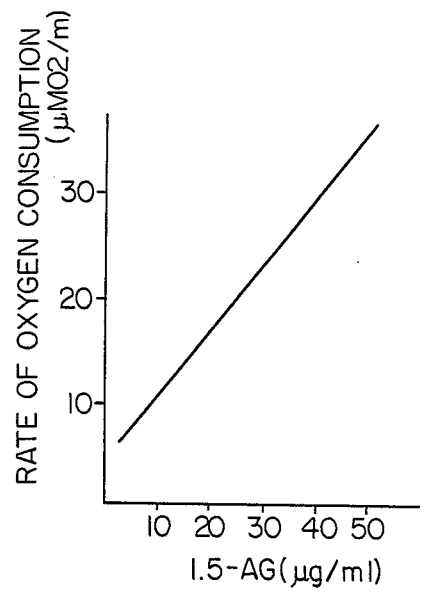
FIG. 3 shows a calibration curve in the oxygen electrode method.

There is no particular limitation to the aqueous solution of specimen used in the present invention as far as it is intended to measure the concentration of 1,5-AG. Examples include cerebrospinal fluid, plasma, serum and urine or, a solution obtained by treating these specimens so as to readily measure the concentration of 1,5-AG.

Any electron acceptor is usable without any particular limitation as long as it participates in the oxidation of 1,5-AG. Examples of the electron acceptor include oxygen, phenazine methosulfate, dichlorophenol-indophenol; ferricyanide compounds such as potassium ferricyanide, sodium ferricyanide, cytochrome C, etc.; coenzymes such as $NAD^+$, $NADP^+$, FAD FMN (flavin mononucleotide), etc. The amount of the electron acceptor to be used is, for example, at least 1 $\mu M$ per 1 in the aqueous solution of specimen, preferably approximately 3 $\mu M$ to 500 mM.

Examples of the reduction products of the electron acceptor include hydrogen peroxide, the reduction product of dichlorophenol-indophenol, ferrocyanide compounds, reduction type cytochrome C, NADH, NADPH, reduction type FMN, etc.

In oxidizing 1,5-AG to the compound represented by formula (1), enzyme is generally utilized, This enzyme is an enzyme capable of oxidizing 1,5-AG to the compound represented by formula (1) (hereafter referred to as "1,5-AG oxidase"). The enzyme having such an ability has been found by the present inventors for the first time and is obtained by microorganisms producing the same. Examples of such microorganisms include Pseudomonas sp. NK-85001 (FERM BP-1037 deposited in the Fermentation Research Institute Agency of Industrial Science and Technology, 1-3, Higashi 1-chome Yatabe-machi Tsukuba-gun Ibaraki-ken 305, Japan), *Pycnoporus coccineus* IFO 4923 and IFO 6490, *Coriolus consors* IFO 9078, *Coriolus versicolor* (IFO 4937), *Daedaleopsis styracina* (IFO 4910), *Gleophyllum sepiarium* (Z-41, NRRL 12506), *Pleurotus ostraetus* (Z-64, NRRL 12507), etc. Of these microorganisms, the microorganism belonging to the genus Pseudomonas is a novel strain isolated from the soil collected by the present inventors in Saitama Prefecture, Omiya-shi, Yoshino-cho, in 1983, June. Bacteriological properties of this strain are as follows.

1. Morphology (cultured in bouillon-agar medium at 27° C. for 16 hours)

1. (1) Size of cell: 0.7–0.8 × 1.0–1.7 μm, rod
(2) Pleomorphism: not recognized
(3) Motility: It possess polar flagella with motility.
(4) Presence or absence of spore: not recognized
(5) Gram staining: negative
(6) Acid fast: negative 2. Growth condition in various media:
(1) Bouillon-agar plate culture: It forms lustrous, opaque and entire circular colonies with brown white color.
(2) Bouillon-agar slant culture: It diffuses and proliferates on the surface of medium to grow opaque and lustrous. The color is brown white.
(3) Bouillon liquid culture: On the first day of culture, it gets turbid as a whole and cells precipitate at the bottom of a test tube on the 3rd day. Pellicle is observed.
(4) Bouillon gelatin stab culture: It grows only on the surface by culture at 20° C. No liquefication of gelatin by culture for 20 days.
(5) Litmus milk: no change 3. Physiological properties (cultured at 27° C.)
(1) Reduction of nitrate: positive
(2) Denitration: positive
(3) MR Test: negative
(4) VP Test: negative
(5) Indole formation: negative
(6) Formation of hydrogen sulfide: negative
(7) Hydrolysis of starch: negative
(8) Utilization of citric acid: It utilizes citric acid in QChristensen's and Simmon's media but not in Kosar's medium.
(9) Utilization of inorganic nitrogen source: It utilizes ammonia but no nitrates.
(10) Formation of pigment: negative
(11) Urease: positive
(12) Oxidase: positive
(13) Catalase: positive
(14) Growth conditions:
10°–37° C.
pH 7–8.5
(15) Behavior to oxygen: aerobic
(16) O-F test: oxidative
(17) Utilization of carbohydrates: It utilizes glucose, glycerin, sodium succinate and sodium citrate but neither sodium acetate nor p-hydroxybenzoic acid.
(18) Formation of acids and gas from sugars:

|  | Formation of Acids | Formation of Gas |
| --- | --- | --- |
| L-Arabinose | + | − |
| D-Xylose | + | − |
| D-Grucose | + | − |
| D-Fructose | + | − |
| D-Galactose | + | − |
| Glycerin | + | − |
| Rhamnose | + | − |
| D-Mannose | − | − |
| Maltose | − | − |
| Sucrose | − | − |
| Lactose | − | − |
| Trehalose | − | − |
| D-Sorbitol | − | − |
| D-Mannitol | − | − |
| Inositol | − | − |
| Raffinose | − | − |
| Starch | − | − |

(19) Resistance to sodium chloride: Sodium chloride was added to basic medium composed of 10 g of tryptone and 1 liter of distilled water at pH 7.0 in concentrations of 2%, 5% and 7%, respectively. After inoculating a bacterial solution thereon, stationary culture was performed. Growth was noted in media of 2% and 5% but no growth was noted in the medium 7%.
(20) Phenyl pyruvate test: negative
(21) Tyrosine solubility: negative Based on the foregoing properties, the taxonomical properties of this strain were compared with the classification in Bergey's Mannual of Determinative Bacteriology, 8th edition (1974); this strain is akin to *Pseudomonas stutzeri* belonging to the genus Pseudomonas at page 220. However, the strain possesses properties that it does not hydrolyze starch and does not produce any acid from maltose and is thus different from *Pseudomonas stutzeri* in these points. From the foregoing reasons, the strain is given *Pseudomonas sp. NK-85001*.

As media for culturing the above-described strain, there may be used media containing 1,5-AG, inorganic nitrogen sources and inorganic salts. For the purpose of accelerating the growth, organic nutrient sources can be supplemented. As the inorganic nitrogen sources, there can be used ammonium sulfate, ammonium chloride, etc. and, salts of sodium, potassium, magnesium, calcium, iron, zinc, etc. can be used as the inorganic salts. As the organic nutrient sources there can be used peptone, Casamino acid, meat extract, corn steep liquor, yeast extract, etc.

It is preferred that culture be performed under aerobic conditions by, such as shaking, aerial agitation, etc. Incubation is performed at pH of 6 to 8 and temperatures of 25° to 35° C.

The 1,5-AG enzyme derived from the genus Pseudomonas which can be used in the present invention is isolated by the following method. Namely, the enzyme is present in a membrane fraction of cells so that the cells are isolated from the culture and destroyed in an appropriate buffer solution and, the membrane fraction is colleced from its treated solution.

To destroy the cells, physical methods such as by means of dyno mill, French press, ultrasonic wave, etc., chemical methods using Triton X-100, EDTA, etc., or enzymatic methods using lysozyme, etc. can be used singly or in combination. The membrane fraction can be obtained in a state of a suspension in which the membrane fraction is separated from the cell wall components, nucleic acids, intracellular soluble proteins, etc. by utilizing a plurality of centrifugal forces.

Subsequently, active components are extracted with membrane fraction-solubilizing agents such as Triton X-100 (polyoxyethylene octyl phenyl ether), cholic acid, deoxycholic acid, etc. to obtain the 1,5-AG oxidase extract. From the extract, the 1,5-AG oxidase can be isolated utilizing methods generally used for purification of enzyme such as polyethylene glycol fractionation, ammonium sulfate fractionation, etc.

Next, properties of the 1,5-AG enzyme derived from the genus Pseudomonas are described below.

1. Activity
It oxidizes 1,5-AG to produce the compound of formula (1) described above.

2. Substrate specificity
It specifically acts on 1,5-AG.

3. Optimum pH
pH 6 to 7.5.

4. Optimum temperature
25° to 41° C.

5. Stable pH 6.5 to 8.

Further the 1,5-AG oxidase derived from the genus Pycnoporus and the genus Coriolus which may be used in the present invention can be isolated by the following method.

Namely, this enzyme is present in the cytoplasm fraction in cells so that the cells are separated from the culture and destroyed in an appropriate buffer solution and, the cytoplasm fraction is obtained from its treated solution.

To destroy the cells, the cells are destroyed in a manner similar to the case of the genus Pseudomonas described above. The cytoplasm fraction can be separated as precipitates from the membrane fraction, cell wall components, etc. by centrufugation of a solution obtained after destruction of the cells.

Subsequently, the supernatant is fractionated in a conventional manner generally used for purification of enzyme, such as polyethylene glycol fractionation, ammonium sulfate fractionation, etc. to isolate the 1,5-AG oxidase. In case that enzyme of higher purity is required, the enzyme can be purified, if necessary, by column chromatography such as gel filtration and ion exchange chromatography, etc. conventionally used.

Next, properties of the 1,5-AG oxidase obtained from the microorganisms belonging to the genus Pycnoporus and the genus Coriolus are shown below.

|  | 1,5-AG Oxidase | |
| --- | --- | --- |
|  | Derived from the genus Pycoporus (IFO 4923) | Derived from the genus Coriolus |
| Action | It oxidizes 1,5-AG to produce the compound of formula (1) or (2) described above. | |
| Substrate Specificity | It oxdizes not only 1,5-AG but also glucose | |
| Optimum pH | 5–6 | 5.0–5.5 |
| Optimum temperature | 37–55 | 35–55 |
| Stable pH | 4–9 | 4–9 |

The 1,5-AG oxidase can be obtained from the microorganisms belonging to the genus Daedaleopsis and the genus Pleurotus in a similar manner.

In the present invention, not only the isolated 1,5-AG oxidase but also the cell-treated products such as the 1,5-AG oxidase extract, the suspension of membrane fraction, etc. can also be utilized. Further, they can be utilized in the form of carriers such as resin, membrane, etc. having immobilized the same thereon.

Next, products produced in the reaction solution by adding 1,5-AG to the solution containing 1,5-AG oxidase such as 1,5-AG oxidase extract and the membrane fraction suspension are described below.

When about 2 mg/ml of 1,5-AG is added to a membrane fraction suspension (concentration of protein, 10 mg/ml; tris-hydrochloride buffer, 0.05M; pH 7) from a microorganism belonging to the genus Pseudomonas and they are reacted at 30° C. for 16 hours with shaking, 1,5-AG disappears but Substance (A) is produced and accumulates. This can be confirmed by TLC analysis. The reaction solution is spotted onto a silica gel plate and developed with a solvent of iso-PrOH:H$_2$O (95:5) and then thoroughly dried. Anisaldehyde sulfate reagent is sprayed thereon and heated at 90° to 100° C. for 5 to 10 minutes, Substance (A) can be observed at Rf of about 0.4 as a blue spot.

The membrane fraction is removed by ultracentrifugation from the reaction solution after the reaction is completed. The supernatant is freeze dried to give white powders. The white powders are dissolved in a small quantity of ethanol and insoluble matters are removed. A 2,4-dinitrophenylhydrazine-saturated ethanol solution and a trace amount of concentrated hydrochloric acid are added to the filtrate. After heating in hot water, the mixture is then cooled and water is added thereto until it gets turbid. The mixture is then allowed to stand to give brown precipitates. The precipitates are taken by filtration, recrystallized from ethanol-water and, if necessary, purified by silica gel chromatography to give yellow brown needles.

Physicochemical properties of the crystals are as follows.

1. Melting point: 192° C.
2. Molecular weight: 342 (mass spectrum).
3. Molecular formula: $C_{12}H_{14}N_4O_8$: Found by mass spectrum: 343 (M+H)$^+$. Calcd.: 342, 272.
4. UV spectrum max. nm ($E_1^{1\%})_{cm}$ (in methanol) 231 (416.2), 255 sh (313.5), 280 sh (178.4), 364 (659.4).
5. IR spectrum IR spectrum of specimen is measured using the tablet method with KBr. 3600~3000 cm$^{-1}$ (broad), 1622, 1584, 1518, 1504, 1415, 1333, 1273, 1224, 1137, 1073, 1050, 1028, 993, 925, 878, 740.

6. $^{13}$CNMR chemical shift

The spectrum is measured in a DMSO-d$_6$ solvent. The chemical shift is determined as a comparative value using 0 ppm as internal standard tetramethylsilan; under the experimental condition, signal of the DMSO-d$_6$ solvent appears at 40.40 ppm. In conformity with the data in the mass spectrum, 12 carbons were observed. 61.9(t), 71.2(t), 73.6(d), 78.4(d), 82.3(d), 116.2(d), 124.0(d), 130.1(s), 130.8(d), 137.6(s), 145.5(s), 153.2(s).

7. $^1$H NMR Spectrum:

The spectrum was measured in DMSO-d$_6$. Chemical shift was a comparative value with data obtained using tetramethylsilane as internal standard of 0 ppm. 3.69 ppm (1H, dd), 4.14~4.15 (2H, ABq), 4.62~4.65 (2H, t, d), 5.63~5.65 (1H, d), 7.24 (1H, broad), 7.87-7.90 (1H, d), 8.33~8.37 (1H, dd), 8.86~8.87 (1H, d), 4.62~4.65 (1H, t—O$\underline{H}$), 5.63~5.65 (1H, d—O$\underline{H}$), 7.24 (1H, br—N$\underline{H}$).

From these data, the aforesaid yellow needles are assumed to have the following chemical formula (3):

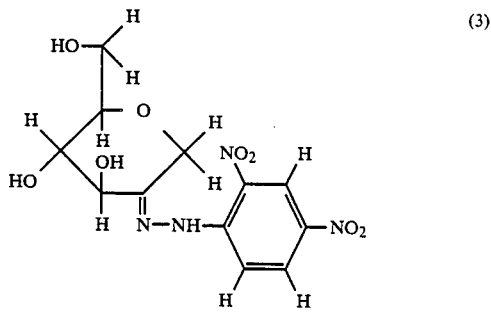

From this, Substance (A) was assumed to possess the aforesaid chemical formula (1).

Further the compound of formula (3) described above was also obtained by treating 1,5-AG using the enzyme obtained from microorganisms belonging to the genus Pycnoporus, the genus Coriolus, the genus Daedaleopsis, the genus Pleourotus and the genus Gloeophyllum in a manner similar to the membrane fraction suspension of the microorganisms belonging to the genus Pseudomonas described above.

Next, to confirm the structure of the product, the compound of formula (1) was chemically synthesized. It has been found that the compound of formula (1) readily hydrates in the presence of water to form the compound of formula (2). This hydrate was reacted in a manner similar to the case where 2,4-dinitrophenyhydrazine was reacted with the treated prodcut of 1,5-AG with the membrane fraction suspension of the microorganisms belonging to the genus Pseudomonas described above, whereby quite the same compound of formula (3) described above was obtained. From this, it is assumed that the product of the 1,5-AG oxidase or the compound of formula (1) would have been present in the form of the hydrate showed by formula (2).

Thus, identification of the product by the 1,5-AG oxidase and the hydrate chemically synthesized was performed by gas chromatography. Both compounds were trimethylsilylated and analyzed by a column, where both were detected at quite the same retention time. Further, analysis of fragment pattern of the peak compound by gas chromatography and mass spectrometry (GC-MS) revealed that quite the same pattern was obtained.

From the foregoing, the above assumption is believed to be correct. Accordingly, it is thought that the enzyme or membrane fraction suspension used in the present invention would catalyze the following reaction:

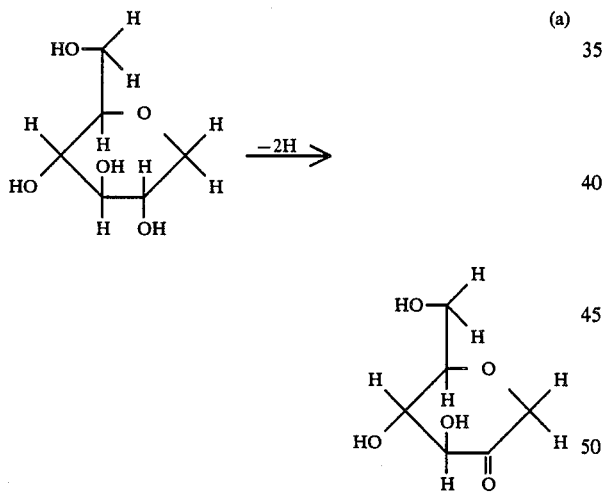

Further it is believed that the reaction in the present invention would follow the reaction equation (a) described above.

Physicochemical properties of the chemically synthesized hydrate of formula (2) are as follows.

1. Thermal analysis (in nitrogen flow):
   Dehydration temperature: 86° C. (weight reduction of 1 molecule of water was noted.
   Melting point: 63°–74° C.
2. Molecular weight: 180 (mass spectrum).
3. Molecular formula: $C_6H_{12}O_6$.
4. IR Spectrum: $\nu_{KBr}^{cm-1}$: 3400, 2950, 2875, 1090, 1040, 840.
5. $^{13}C$-NMR (100 MHz); $\delta_{ppm}^{D2O}$: 93.45(s), 81.47(d), 77.75(d), 72.56(t), 69.85(d), 62.03(t).
6. $^1H$-NMR (400 MHz) $\delta_{ppm}^{D2O}$: 3.89 (1H, dd), 3.75 (1H, d), 3.67 (1H, dd), 3.56 (1H, d), 3.45 (1H, d), 3.44 (1H, t), 3.40 (1H, m).
7. Crystalline form: amorphous white powders.

The compounds of formulae (1) and (2) are novel compounds. Further the reaction in which 1,5-AG is dehydrogenated to produce the compound of formula (1) is also a novel reaction.

The method of measurement of 1,5-AG of the present invention is based on the above reaction. Utilizing the reaction progress or reaction products, various measurements can be made and their contents are described below.

(1) Method based on consumption of oxygen

In a sealed type reactor are charged 1 ml of 0.05M tris-hydrochloride buffer (pH 7.0), 20 μl of 30 mM phenazinemethosulfate and 0.3 ml of solution or suspension containing 1,5-AG oxidase. Oxygen electrodes are inserted in the reaction mixture. While stirring the content of the reactor at 34° C., 50 μl of a 1,5-AG solution is added thereto to initiate the reaction. The amount of oxygen consumed is measured with an oxygen monitor with the passage of time. Using 1,5-AG solutions having known concentrations, a calibration curve is prepared and the concentration of 1,5-AG is calculated from the amount of oxygen consumed.

(2) Method utilizing color change of electron acceptor:

In a reactor are charged 0.7 ml of tris-hydrochloride buffer (0.05M, pH 7), 0.1 ml of a 0.1M potassium ferricyanide solution, 0.1 ml of 1,5-AG oxidase obtained from the microorganism belonging to the genus pseudomonas or an extract thereof and 0.1 ml of a 1,5-AG solution. After reacting at 34° C. for 10 minutes, 0.5 ml of a ferric sulfate-dupanol reagent (5 g of ferric sulfate, 3 g of sodium laurylsulfate, 95 ml of 85% phosphoric acid and 900 ml of distilled water) and 3.5 ml of distilled water are added to the mixture followed by allowing to stand for 10 minutes. Then, absorbance is measured at 660 nm. Using 1,5-AG solutions having known concentrations, a calibration curve is prepared and the concentration of 1,5-AG is calculated from the absorbance of the specimen.

As electron acceptors, there can be used dichlorophenol-indophenol, etc., in addition to ferricyanides such as potassium ferricyanide, sodium ferricyanide, ammonium ferricyanide, etc.

(3) Method of detecting $H_2O_2$:

In a reactor are charged 0.3 ml of sodium phosphate buffer (1/15M, pH 5.6), 0.5 ml of a hydrogen peroxide detecting solution containing substrate for horse raddish peroxidase (e.g., 4 mM of 2,2'-azino-di-[3-ethylbenzothiazoline sulfonate (6)] (ABTS)) and 12 u/ml of horse raddish peroxidase, 0.1 ml of 1,5-AG oxidase and 0.1 ml of a specimen solution containing 1,5-AG. After reacting at 37° C. for 30 minutes, the reaction is stopped under ice cooling and the absorbance is measured at 405 nm. Using 1,5-AG solutions having known concentrations, a calibration curve is prepared and the concentration of 1,5-AG is calculated from the absorbance of the specimen.

As substrates for horse raddish peroxidase, there can be utilized, in addition to ABTS, color-forming substrates such as 5-aminosalicylic acid, 4-aminoantipyrine and phenol, o-toluidine, etc., and fluorescent substrates such as p-hydroxyacetic acid, p-hydroxypropionic acid, etc.

Further for detecting $H_2O_2$ produced in the oxidation reaction of 1,5-AG, a method for directly measuring $H_2O_2$ using $H_2O_2$ electrodes, a method utilizing chemical luminescence generated by oxidation of lucigenine, aryl oxalates, etc. with $H_2O_2$ may also be utilized in addition to the above method.

(4) Method of quantitative assay for the compound of formula (1) or the compound of formula (2):

The membrane fraction suspension derived from bacteria of the genus Pseudomonas is added to a 1,5-AG solution followed by reacting at 30° C. for 16 hours. After completion of the reaction, the membrane fraction is removed by ultracentrifugation and the supernatant is freeze dried to give white powders. The powders are treated with a labeling agent for the carbonyl group or a protecting agent for the hydroxy group to effect the assay. In the case of using, e.g., 2,4-dinitrophenylhydrazine, as the labeling agent for the carbonyl group, the freeze dried powders are dissolved in a small quantity of ethanol and insoluble matters are removed; a saturated ethanol solution of 2,4-dinitrophenylhydrazine and a trace amount of concentrated hydrochloric acid are added to the filtrate followed by reacting in hot water with heating. By analysis of the product by means of reversed phase HPLC (liquid chromatography), the product of formula (1) can be detected. Further in the case of using trimethylsilylchloride (TMS) as the protecting agent for the hydroxy group, the freeze dried powders are dissolved in a small quantity of pyridine and TMS is then added to the solution. By stirring the mixture at room temperature, a compound wherein all hydroxy groups of the product of formula (2) are protected is obtained. By analysis of a part of the solution by gas chromatography, the compound of formula (2) can be quantitatively determined.

[Reagent for analysis]

The reagent for analysis of the present invention is a reagent comprising at least the enzyme of the present invention. Namely, its form is not limited but the enzyme may be a soluble enzyme of a solution, freeze dried, powdery or granular type. Further, the enzyme may be immobilized enzyme immobilized onto carriers of a membrane, gel, particulate, microcapsular, tubular or container type, in various manners. In addition to the enzyme of the present invention, the reagent may be supplemented with buffers such as liquid or powdery phosphate buffer, tris-hydrochloride buffer, acetate buffer, citrate buffer, veronal buffer, etc.; salts (sodium chloride, etc.), sugars that do not react with the enzyme of the present invention (sucrose, etc.); polyvalent alcohols (glycerol, propylene glycol, sorbitol, etc.); coenzymes (FAD, etc.); and other appropriate stabilizers, surfactants, etc.

Upon analysis of 1,5-AG, the reagent for analysis described above is used so as to obtain a necessary enzyme activity depending upon the aforesaid various methods for detection. Further, an amount of the reagent appropriate for each of the detection methods may be previously sealed in a container such as a reagent bottle, ampoule, etc.

[Kit for analysis]

The kit for analysis is composed of the aforesaid reagent for analysis comprising the enzyme of the present invention and reagents for detection which are reagents for detecting the reaction caused by the enzyme of the present invention. The reagent for detection refers to an electron acceptor per se that participates in the oxidation of 1,5-AG accompanied by color formation or to reagents that is necessary for detection of one of the 1,5-AG oxidation reaction products as an index of the 1,5-AG oxidation. As examples of the latter, in the case of using hydrogen peroxide as the index, examples of the reagents for detection include combination of peroxidase or a peroxidase-like substance and its color forming substrate or color forming substrate and a coupler, combination of peroxidase or a peroxidase-like active substance and its fluorescent substrate, combination of peroxidase or a peroxidase-like active substance and a luminescence forming reagent, etc. Specific examples of these reagents are clear from the description entitled "Method for detecting $H_2O_2$" described above.

Further similarly in the case of using the compound of formula (1) or the compound of formula (2), the oxidation products of 1,5-AG, as the index, reagents necessary for detection are combined with the reagent for analysis comprising the enzyme of the present invention and the combination can be constructed as the kit for analysis. The reagent for analysis comprising the enzyme of the present invention and the aforesaid reagents for detection may all be mixed together to form a single reagent; alternatively, in case that mutually interfering components are present, each component may be separated so as to form an appropriate combination. Further these components may be prepared in the form of a solution or powders. Furthermore, they may be incorporated into an appropriate support such as a film to prepare into a test paper sheet or an analysis film.

The kit for analysis of the present invention may further contain, in addition to the combinations described above, pretreatment reagents for selectively removing contaminants, standard reagents containing a definite amount of 1,5-AG, etc.

Preferred examples of the kit for analysis of the present invention include a kit for detecting 1,5-AG by spectroscopic detection of the reduction product of a ferricyanide as an electron acceptor and a kit for analysis of 1,5-AG by spectroscopic detection of hydrogen peroxide.

In the case of the kit using the ferricyanide as an electron acceptor, the enzyme is used more than 0.2 units/test and ferricyanide is used more than 5-fold moles, preferably more than 10-fold moles of 1,5-AG and usually $10^{-5}$ mol/test of potassium ferricyanide is used.

In the case of the kit for spectroscopically detecting hydrogen peroxide, the enzyme is used more than 0.2 units/test, peroxidase is used 1–10 unit/test and substrate for color formation is used more than 5-fold moles, preferably more than 10-fold moles of hydrogen peroxide produced in the oxidation of 1,5-AG and usually $5 \times 10^{-7}$ to $5 \times 10^{-6}$ mols/test of ABTS is used as a substrate for color formation.

Next, the effects of the present invention will be described below.

TEST EXAMPLE 1 (substrate specificity)

In order to examine substrate specificity, the reaction was performed in the ferricyanide method described above using the 1,5-AG oxidase extract obtained in Reference Example 1 later described except that the substrate was replaced by sugar and sugar alcohol. As a result, the 1,5-AG oxidase produced by the microorganism belonging to the genus Pseudomonas shows high specificity to 1,5-AG as shown in Table 1.

TABLE 1

| Substrate Specificity | |
|---|---|
| Substrate | Relative Reactivity (%) |
| 1,5-AG | 100 |
| Glucose | 6 |
| Galactose | 3 |
| Sorbose | 6 |
| Xylose | 3 |
| Sorbitol | 1 |
| Mannitol | 2 |
| Xylitol | 3 |
| Arabitol | 6 |
| Erythritol | 2 |
| Glucosamine | 3 |
| Gluconic acid | 2 |

TEST EXAMPLE 2 (optimum pH and temperature conditions)

Using the extract obtained in Reference Example 1 described later, the optimum pH and the optimum temperature of the 1,5-AG oxidase produced by the microorganism belonging to the genus Pseudomonas in the conversion reaction of 1,5-AG were examined to give the results shown in FIGS. 1 and 2. These figures reveal that the optimum pH and optimum temperature are approximately pH 6 to 7.5 and 25° to 41° C., respectively.

Further in order to examine pH stability, the extract was added to phosphate buffer (pH 6 to 7) and tris-hydrochloride buffer (pH 7.2 to 9) having different pH values. After storing at 4° C. for 1 day, the conversion activity was examined; it was stable in the pH range of 6.5 to 8.

TEST EXAMPLE 3 (measurement of 1,5-AG)

(1) Calibration curve by the oxygen electrode method

The extract (protein concentration: 5 mg/ml) obtained in Reference Example 1 later described was used. The following reaction solution was added to a reactor of an oxygen densitometer (Oxygraph manufactured by Guilsol Co. in America) and kept at 34° C. while agitating.

| | |
|---|---|
| Tris-hydrochloride buffer (0.05 M, pH 7) | 1 ml |
| Solubilizing solution (protein content, 5 mg/ml) | 0.3 ml |
| 30 mM Phenazine methosulfate | 20 μl |

After the reactor was stoppered and sealed, 50 μl of 1,5-AG solutions having known concentrations were injected into the reactor using a microsyringe and, a rate of oxygen consumed was recorded. As a result, a proportional relationship was noted between the 1,5-AG concentration and the rate of oxygen consumed, as shown in FIG. 3.

(2) Calibration curve in the method using a ferricyanide as an electron acceptor The extract (protein content, 5 mg/ml) obtained in Reference Example 1 later described was used. A reaction solution having the following composition was reacted at 34° C. for 10 minutes in a test tube.

| | |
|---|---|
| Tris-hydrochloride (0.05 M, pH 8) | 0.7 ml |
| Potassium ferricyanide solution (0.1 M) | 0.1 ml |
| Extract | 0.1 ml |
| 1,5-AG Solution | 0.1 ml |

(Distilled water was used for blank)

Figure 4:
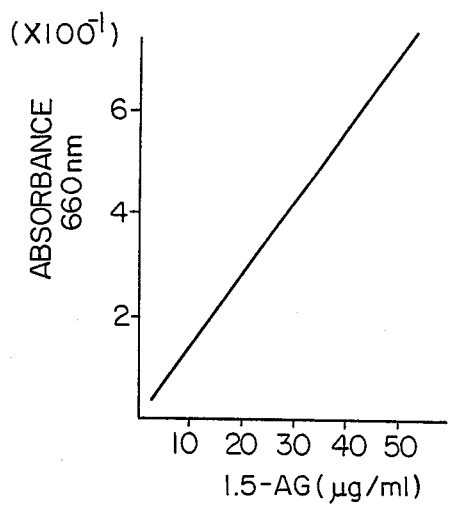
FIG. 4 shows a calibration curve in the ferricyanide method.

After the reaction, 0.5 ml of ferric sulfate-dupanol reagent and 3.5 ml of distilled water were added to discontinue the reaction. The system was allowed to stand for 10 minutes, where the system was colored green. At this stage the absorbancy was measured at 660 nm. When tested using the 1,5-AG solutions having known concentrations, a proportional relationship in absorbance was noted between the 1,5-AG concentration and the absorbance at 660 nm, as shown in FIG. 4.

(3) Calibration curve in the method using dichlorophenolindophenol (DCIP) as an electron acceptor The extract (protein content, 5 mg/ml) obtained in Reference Example 1 later described was used. A reaction solution having the following composition was charged in a cell of a spectrophotometer and kept at 34° C.

| | |
|---|---|
| Tris-hydrochloride buffer (0.05 M, pH 8) | 1.8 ml |
| 1 mM DCIP | 0.3 ml |
| 10 mM KCN | 0.3 ml |
| Extract | 0.3 ml |

The 1,5-AG solution kept at 34° C. was charged in the cell and the absorbance at 600 nm was recorded while stirring with the passage of time.

Figure 5:
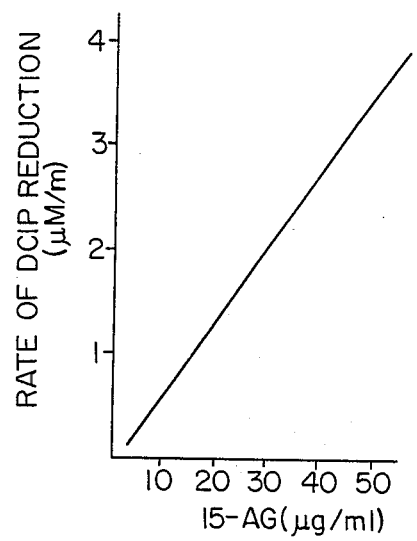
FIG. 5 shows a calibration curve in the dichlorophenol-indophenol method.

When tested with 1,5-AG having known concentrations, a proportional relationship was noted between the 1,5-AG concentration and the rate of change in the absorbance at 600 nm, i.e., the reduction rate of DCIP, as shown in FIG. 5.

(4) Calibration curve in the method for detecting $H_2O_2$ by color formation

The enzyme (enzyme activity, 3.2 u/ml) obtained in Reference Example 6 later described was used. A reaction solution having the following composition was reacted at 37° C. for 2 hours in a test tube.

| | |
|---|---|
| Sodium phosphate buffer (1/15 M, pH 5.6) | 0.3 ml |
| Color forming reagent: aforesaid phosphate buffer containing 4 mM ABTS and 12 u/ml of peroxidase | 0.5 ml |
| Enzyme | 0.1 ml |
| 1,5-AG Solution | 0.1 ml |

(Distilled water was used for blank)

Figure 6:
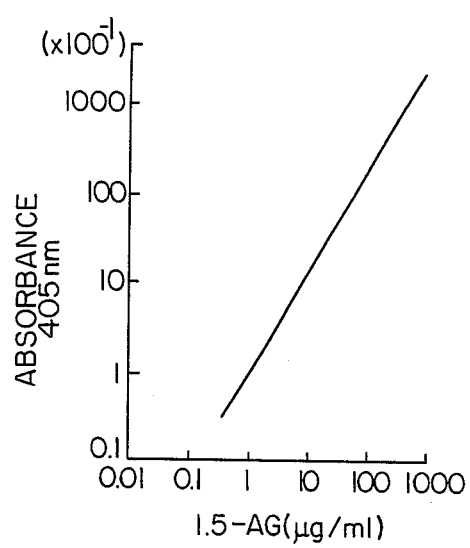
FIG. 6 shows a calibration curve in the $H_2O_2$ colorimetry.

After the reaction, the system was ice cooled to discontinue the reaction and the absorbance was measured at 405 nm. When tested using 1,5-AG solution having known concentrations, a proportional relationship was noted between the 1,5-AG concentration and the absorbance at 405 nm, as shown in FIG. 6.

(5) Calibration curve in the method for detecting $H_2O_2$ by fluorescence

The enzyme (enzyme activity, 1.5 u/ml) obtained in Reference Example 6 later described was used. A reaction solution having the following composition was reacted at 37° C. for 2 hours in a test tube.

| | |
|---|---|
| Fluorescent reagent sodium acetate buffer (0.05 M, pH 5.0) containing 0.1% of p-hydroxyphenylpropionic acid and 4 u/ml of peroxidase | 0.2 ml |
| Enzyme | 0.1 ml |
| 1,5-AG Solution | 0.1 ml |

(Distilled water was used for blank)

After the reaction, 2.5 ml of sodium glycine buffer (0.1M, pH 10.3) was added to the system to discontinue the reaction. A relative fluorescent intensity was measured at excited wavelength of 315 nm and fluorescent wavelength of 450 nm.

Figure 7:
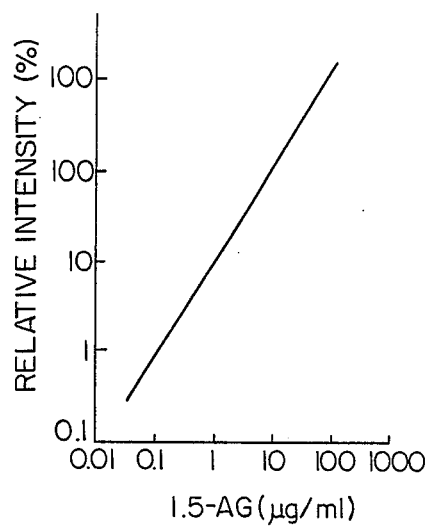
FIG. 7 shows a calibration curve in the $H_2O_2$ fluorometry.

When tested with 1,5-AG solution having known concentrations, a proportional relationship was noted between the 1,5-AG concentration and the relative fluorescent intensity, as shown in FIG. 7.

(6) Calibration curve in the $H_2O_2$ electrode method

Figure 8:
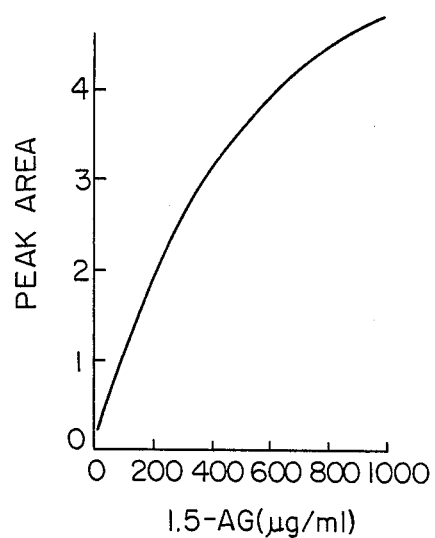
FIG. 8 shows a calibration curve in the $H_2O_2$ electrode method.

In the column having immobilized thereto 1,5-AG oxidase obtained in Reference Example 7 later described, a pump injector and $H_2O_2$ electrodes (Ishikawa Seisakusho, Ltd., BH type) were connected at the up stream to the down stream, respectively. The $H_2O_2$ electrodes were set with a hydrogen peroxide meter (Ishikawa Seisakusho, Ltd., Model AI-10006) and a recorder. The 1,5-AG immobilized column and the $H_2O_2$ electrodes were dipped in a water bath with thermostatt kept at 37° C. Through the pump phosphate buffer (1/15M, pH 5.6) was flown at a rate of 1 ml/min to stabilize. Into the flow path, 50 μl of the 1,5-AG solution was flown through the injector and the peak area on the recorder produced by the oxidation of 1,5-AG was measured. When tested with 1,5-AG solutions having known concentrations, a calibration curve as shown in FIG. 8 was obtained between the 1,5-AG concentration and the peak area.

As is evident from the foregoing, 1,5-AG can be quantitatively determined in an extremely manner in accordance with the present invention.

EXAMPLE 1

With respect to a specimen having the following composition, the 1,5-AG content was measured by 3 methods described below. As shown below, it was possible to measure 1,5-AG by the respective methods.

| Composition of specimen solution: | |
|---|---|
| 1,5-AG | 100 μg/ml |
| Glucose | 1000 μg/ml |
| Sorbitol | 1000 μg/ml |

| Method | Found Value of 1,5-AG |
|---|---|
| Enzyme electrode method | 109 μg/ml |
| Ferricyanide method | 107 μg/ml |
| DCIP method | 98 μg/ml |

EXAMPLE 2

To 0.4 ml of human serum was added 30 μl of a perchloric acid aqueous solution (60% w/v). After shaking, the mixture was centrifuged and 0.2 ml of the resultant supernatant was passed through a pretreatment column packed with 0.8 ml of borate type strongly basic resin AG1-X-8 (manufactured by Bio-Rad Co., Ltd.), which was washed with 3 ml of water to give 3 ml of a passed liquid. After 3 ml of the column-passed liquid was concentrated to dryness, distilled water was added thereto to accurately adjust to 0.5 ml. The thus obtained specimen from which protein had been removed and to which the pretreatment had been subjected was measured by the 3 methods for detecting $H_2O_2$ shown in Test Example 3 described above. As shown below, it was possible to measure 1,5-AG in serum by the respective methods. Each calibration curve was prepared by treating standard solutions containing known concentrations of 1,5-AG in quite the same manner as described above and measuring by each method.

| Method | Found Value* of 1,5-AG in Serum |
|---|---|
| Detection of color of $H_2O_2$ | 28.0 μg/ml |
| Detection of fluorescence of $H_2O_2$ | 27.6 μg/ml |
| $H_2O_2$ Electrode method | 30.4 μg/ml |

*The value found in the gas chromatograpy was 28.5 μg/ml.

REFERENCE EXAMPLE 1

Harvest of membrane fraction having 1,5-AG oxidase derived from the microorganism belonging to the genus Pseudomonus In a Erlenmeyer's flask of a 500 ml volume was charged 100 ml each of medium composed of 1% of Casamino acid, 0.2% of 1,5-AG, 0.1% of $(NH_4)_2SO_4$, 0.1% of $K_2HPO_4$, 0.1% of NaCl, 0.02% of $MgSO_4.7H_2O$, 0.1% of yeast extract and distilled water and adjusted to pH 7. After sterilizing the medium at 115° C. for 15 minutes, a platinum loop of the culture obtained by slant culture of Pseudomonas sp. NK-85001 [Ferm BP-1037 deposited in the Fermentation Research Institute Agency of Industrial Science and Technology, 1-3, Higashi 1-chome Yatabe-machi Tsukuba-gun Ibaraki-ken 305, Japan] was inoculated in the medium followed by culturing at 30° C. for 16 hours on a rotary shaking culture machine (220 rpm). The cells were separated from the culture solution by centrifugation and washed with tris-hydrochloride buffer (0.05M, pH 7) to give a cell suspension of a 1/10 volume based on the amount of the starting solution. The cell suspension was cooled and destroyed with a French press to give the cell-destroyed suspension. The suspension was centrifuged for 10 minutes (10,000×g). After the precipitated cell walls were removed, centrifugation was continued for further 1 hour (100,000×g) to give the precipitates. The precipitates were washed with tris-hydrochloride buffer (0.05M, pH 7) and suspended in the same buffer to give a membrane fraction suspension. Triton X-100 was added to the suspension in a concentration of 1% (w/v). After agitating at 4° C. for 1 hour, the insoluble matters were removed by centrifugation (100,000×g) to give the 1,5-AG oxidase extract.

REFERENCE EXAMPLE 2

While cooling the active component-solubilized solution obtained in Reference Example 1, ammonium sulfate powders were added thereto. The precipitated protein was separated by centrifugation (10,000×g, 10 minutes) and the activity was measured by ferricyanide method described in the specification. It was noted that the activity was mainly recovered in the 40% ammonium sulfate-saturated fraction.

|  | Specific Activity* |
|---|---|
| Membrane fraction suspension | 0.23 |
| Extract | 0.47 |
| 40% Ammonium sulfate-saturated fraction | 0.85 |
| 60% Ammonium sulfate-saturated fraction | 0 |
| 80% Ammonium sulfate-saturated fraction | 0 |

*A value per 1 mg of protein calculated based on 1 unit of enzyme which is defined to be activity of reducing 2 μmoles of ferricyanide for 10 minutes.

REFERENCE EXAMPLE 3

Harvest of 1,5-AG oxidase derived from *Pycnoporus coccineus* IFO 4923

In an Erlenmeyer's flask of a 500 ml volume was charged 100 ml each of medium composed of 0.3% of 1,5-AG, 0.4% of yeast extract, 0.5% of malt extract and tap water. After sterilization at 115° C. for 15 minutes, one platinum loop of the slant culture of *Pycnoporus coccineus* IFO 4923 was inoculated on the medium followed by culturing at 27° C. for 6 days on a rotary shake culture machine (220 ppm). The cells were separated from the culture solution by centrifugation and washed with sodium phosphate buffer (0.1M, pH 6) to form a cell suspension of a 7.5-fold volume of the wet weight of the cells. The cell suspension was cooled and destroyed with a French press to give the cell-destroyed liquid. The liquid was centrifuged (10,000×g) for 10 minutes under cooling. After the precipitated cell walls were removed, centrifugation was continued for further 1 hour (100,000×g) to remove membrane fraction and obtain the cytoplasm supernatant. Under cooling, ammonium sulfate powders were added to the supernatant and the mixture was agitated to dissolve. The precipitated protein in this case was separated by centrifugation (10,000×g, 10 minutes) and the activity of 1,5-AG oxidase was measured with each ammonium sulfate fraction by the method for detecting $H_2O_2$ described in the specification (wherein a 1,5-AG solution having a 1% concentration was used) and it was noted that the activity was present mainly in the 40–60% ammonium sulfate-saturated fraction. When one unit of enzyme is defined to be an amount that oxidizes 1,5-AG to produce 1 μmole/min of $H_2O_2$, the specific activity of the ammonium sulfate fraction is 4.0. Enzyme of 11 units are obtained per 1 g of the wet cells.

REFERENCE EXAMPLE 4

The strain was changed to *Pycnoporus coccineus* IFO 6490 in Reference Example 3 and cultured in medium having the same composition as in Reference Example 3 for 4 days. The same procedure for purification as in Reference Example 3 was performed to give 1,5-AG oxidase having a specific activity of 3.6.

REFERENCE EXAMPLE 5 (Collection of 1,5-AG oxidase derived from *Coriolus consors* IFO 9078)

The strain was changed to *Coriolus consors* IFO 9078 in Reference Example 3 and cultured in medium having the same composition as in Reference Example 3 for 10 days. The same procedure for purification as in Reference Example 3 was performed to give 1,5-AG oxidase extract having a specific activity of 2.8.

REFERENCE EXAMPLE 6 (Harvest of highly pure enzyme)

A solution of the 60% ammonium sulfate-saturated precipitate of 1,5-AG oxidase obtained in Reference Example 3 in distilled water was used. All of the procedures including chomatography using DEAE-Toyopearl (manufactured by Toyo Soda Mfg. Co., Ltd.) for purification were performed under cooling at 4° C. A 4100 units of enzyme/20 ml of the solution was dialyzed to a 100-fold volume of phosphate buffer (0.01M, pH 6.0) and charged in DEAE-Toyopearl column (2.5 cm×40 cm) equilibrated with the same buffer. After thoroughly washing the column with phosphate buffer (0.01M, pH 6.0), elution was performed with a density gradient of 0.01M to 0.5M using phosphate buffer. The active fraction was eluted in the concentrations between 0.1M and 0.2M and therefore, the active fractions were collected and concentrated using pM 10 ultrafiltration membrane (manufactured by Amicon Co., Ltd.) to give 6.5 ml of the enzyme solution (360 units/ml) showing the specific activity of 18.

REFERENCE EXAMPLE 7 (Production of immobilized column)

In a conventional manner, 0.5 g of a porous glass, CPG-10 (200/400 mesh, mean pore size of 500 Å, manufactured by Electronucleonic Co., Ltd.) was subjected to a coupling treated using 0.5 g of γ-aminopropyltriethoxysilane followed by carboxylation with 0.5 g of succinic anhydride. The dried porous glass was treated with an excess of thionyl chloride in chloroform to convert the carboxyl groups into the acid chloride. To 1 g of the thus obtained acid chloridated porous glass was added 2.5 ml of the 1,5-AG oxidase solution prepared in Reference Example 6 described above. While keeping pH at 6 to 7, the reaction was performed at 25° C. for 12 hours while mildly agitating to complete the condensation reaction. The obtained 1,5-AG oxidase-immobilized porous glass was filled up in a column (1 ml of a syringe) having an inner diameter of 2.3 mm and a length of 70 mm. Through the column 20 ml of phosphate buffer (1/15M, pH 5.6) containing 1M table salt was passed to remove the enzyme not bound covalently. Further the column was washed by passing phosphate buffer (1/15M, pH 5.6) therethrough to give the 1,5-AG oxidase-immobilized column.

What is claimed is:

1. A method of quantitative assay for 1,5-anhydroglucitol which comprises oxidizing 1,5-anhydroglucitol with the enzyme 1,5-anhydroglucitol oxidase in an aqueous solution of a specimen in the presence of an electron acceptor to produce a compound represented by formula (1) below or a hydrate thereof represented by formula (2) below and quantitatively determining 1,5-anhydroglucitol by measuring the amount of said electron acceptor consumed in said aqueous solution of a specimen, by measuring the amount of the reduction product of said electron acceptor produced or by measuring the amount of an oxidized product of 1,5-anhydroglucitol represented by formula (1) below or formula (2) below:

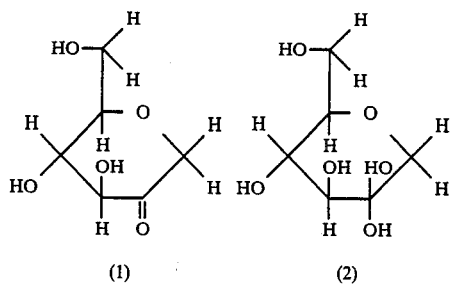

(1)  (2)

2. The method of claim 1 wherein said electron acceptor is oxygen, phenazine methosulfate, dichlorophenolindophenol, a ferricyanide compound, cytochrome C, NAD+, NADP+, FAD or FMN.

3. The method of claim 1 wherein said quantitative assay is made based on the reduction product of said electron acceptor.

4. The method of claim 3 wherein said reduction product of the electron acceptor is hydrogen peroxide.

5. The method of claim 4 wherein a hydrogen peroxide-detecting solution containing horseradish peroxidase and a substrate thereof is used.

6. The method of claim 5 wherein said substrate of horseradish peroxidase is 3,3′,5,5′-tetramethylbenzidine, o-phenylenediamine, 2,2′-azino-di-[3-ethylbenzothiazoline sulfonate], 5-aminosalicylic acid, 4-aminoantipyrine, phenol, o-toluidine, p-hydroxyacetic acid or p-hydroxypropionic acid.

7. A kit for the quantitative assay of 1,5-anhydroglucitol as claimed in claim 1 said kit comprising a reagent for analysis comprising an enzyme 1,5-anhydroglucitol oxidase, and reagents for detecting the reaction caused by the enzyme.

* * * * *